(12) United States Patent
Toplack et al.

(10) Patent No.: US 7,723,516 B2
(45) Date of Patent: May 25, 2010

(54) METHOD FOR THE TREATMENT OF TRIAZINE-CONTAINING WATER OF A MELAMINE PLANT

(75) Inventors: Paul Toplack, Graz (AT); Peter Weiss, Pasching (AT); Hartmut Bucka, Eggendorf (AT)

(73) Assignee: AMI Agrolinz Melamine International GmbH, Linz (AT)

( * ) Notice: Subject to any disclaimer, the term of this patent is extended or adjusted under 35 U.S.C. 154(b) by 650 days.

(21) Appl. No.: 11/665,795

(22) PCT Filed: Oct. 19, 2005

(86) PCT No.: PCT/EP2005/011373

§ 371 (c)(1),
(2), (4) Date: Apr. 19, 2007

(87) PCT Pub. No.: WO2006/042760

PCT Pub. Date: Apr. 27, 2006

(65) Prior Publication Data

US 2009/0062535 A1    Mar. 5, 2009

(30) Foreign Application Priority Data

Oct. 20, 2004  (DE)  ........................ 10 2004 051 432

(51) Int. Cl.
C07D 251/62 (2006.01)
C07D 251/60 (2006.01)
(52) U.S. Cl. ..................................... 544/203; 544/201
(58) Field of Classification Search ................. 544/203, 544/201
See application file for complete search history.

(56) References Cited

U.S. PATENT DOCUMENTS

| 3,423,411 A | 1/1969 | Dakli et al. |
| 3,496,176 A | 2/1970 | Kennedy |
| 6,891,040 B2 * | 5/2005 | Noe' et al. ................. 544/201 |

FOREIGN PATENT DOCUMENTS

| DE | 1930844 A1 | 1/1970 |
| IT | 01282369 B1 | 3/1998 |
| WO | 0071525 A1 | 11/2000 |
| WO | 0146159 A2 | 6/2001 |
| WO | 02100839 A1 | 12/2002 |

* cited by examiner

*Primary Examiner*—Venkataraman Balasubramanian
(74) *Attorney, Agent, or Firm*—The Webb Law Firm

(57) ABSTRACT

The invention relates to a method for treating triazine-containing water of a melamine plant. The method is characterized in that the water containing ionic and non-ionic triazines in a dissolved form is fed to at least one membrane filtration unit, the water is separated into an ionic triazine-rich fraction and a non-ionic triazine-rich fraction in the membrane filtration unit, whereupon the ionic triazine-rich fraction is discharged and the non-ionic triazine-rich fraction is redirected into the melamine plant. The inventive method allows a great portion of the melamine contained in the triazine-containing water to be redirected into the process while the yield is increased along the entire melamine process. Furthermore, the need for fresh water in the wet part of the melamine plant is decreased. The disclosed method can be carried out continuously and in liquid phase.

23 Claims, 2 Drawing Sheets

METHOD FOR THE TREATMENT OF TRIAZINE-CONTAINING WATER OF A MELAMINE PLANT

BACKGROUND OF THE INVENTION

1) Field of the Invention

The invention relates to a process for treating triazine-containing water of a melamine plant, and to a high-pressure process for preparing melamine from urea.

2) Description of the Related Art

The starting material used for melamine preparation is virtually exclusively urea, which is converted to melamine either in a catalytic low-pressure process or in a high-pressure process without catalyst.

The by-products, degradation products and unconverted starting materials present in the crude melamine have to be removed from the product in the subsequent melamine workup. Since the melamine workup is usually effected in the presence of water, these by-products are obtained as wastewater constituents, for example as constituents of the mother liquor from the melamine crystallization.

The wastewater constituents from the melamine process are mainly cyclic nitrogen compounds in the form of triazines such as melamine or ureidomelamine, or oxoaminotriazines (OATs) such as ammeline or ammelide. In addition, urea or cyanuric acid may also be present. Owing to the aqueous melamine workup in a basic medium, these substances are for the most part present in ionic form. Further ionic constituents which may occur in the melamine wastewater are, for example, carbonates, sodium or ammonium ions.

For the purposes of a maximum melamine yield, it is desirable to recover the melamine present in the water and to recycle it into the melamine process very substantially and selectively. This causes a separation of the melamine from the other wastewater constituents.

The prior art discloses some processes for treating triazine-containing melamine wastewaters, which separate the melamine from the OATs. In some of these processes, the OATs are recovered as solids.

According to WO 01/46159 A2, the mother liquor comprising melamine and OATs is acidified up to pH=7 after the melamine crystallization, which forms an OAT suspension which is then subjected to a tangential filtration. This affords an aqueous melamine solution and an OAT dispersion. While the aqueous melamine solution is recycled into the process, the OATs are separated from the dispersion. One disadvantage in this process is that a stream comprising solids is filtered; as a result, there is the risk of filter blockage.

According to IT 0 128 2369, the wastewater comprising melamine and OAT is treated at high temperature and high pressure, which brings about destruction of the OATs. After the $NH_3$ and $CO_2$ formed in this destruction have been stripped out, the remaining solution is recycled into the melamine plant. In this process, there is the disadvantage that not only the OATs but also the melamine present in the wastewater are destroyed in the thermal treatment, and a satisfactory melamine yield in the overall process accordingly cannot be achieved.

WO 02/100839 A1 describes a process in which a majority of the mother liquors of the melamine crystallization are recycled untreated into the melamine plant; $NH_3$ and OAT are recovered from the smaller portion of the mother liquors. The disadvantage of this process is that more fresh water additionally has to be supplied when the untreated, OAT-containing mother liquors are recycled into the melamine process in order to be able to work up the crude melamine melt to the desired quality.

SUMMARY OF THE INVENTION

It is accordingly an object of the invention to develop a process for wastewater treatment, in which it is possible to work in the liquid phase and in which a good separation between melamine and other wastewater constituents is achieved, so that a maximum amount of melamine can be recycled into the process.

BRIEF DESCRIPTION OF THE DRAWINGS

The invention will be illustrated in drawings with reference to working examples as follows.

DETAILED DESCRIPTION OF THE INVENTION

Figure 1:
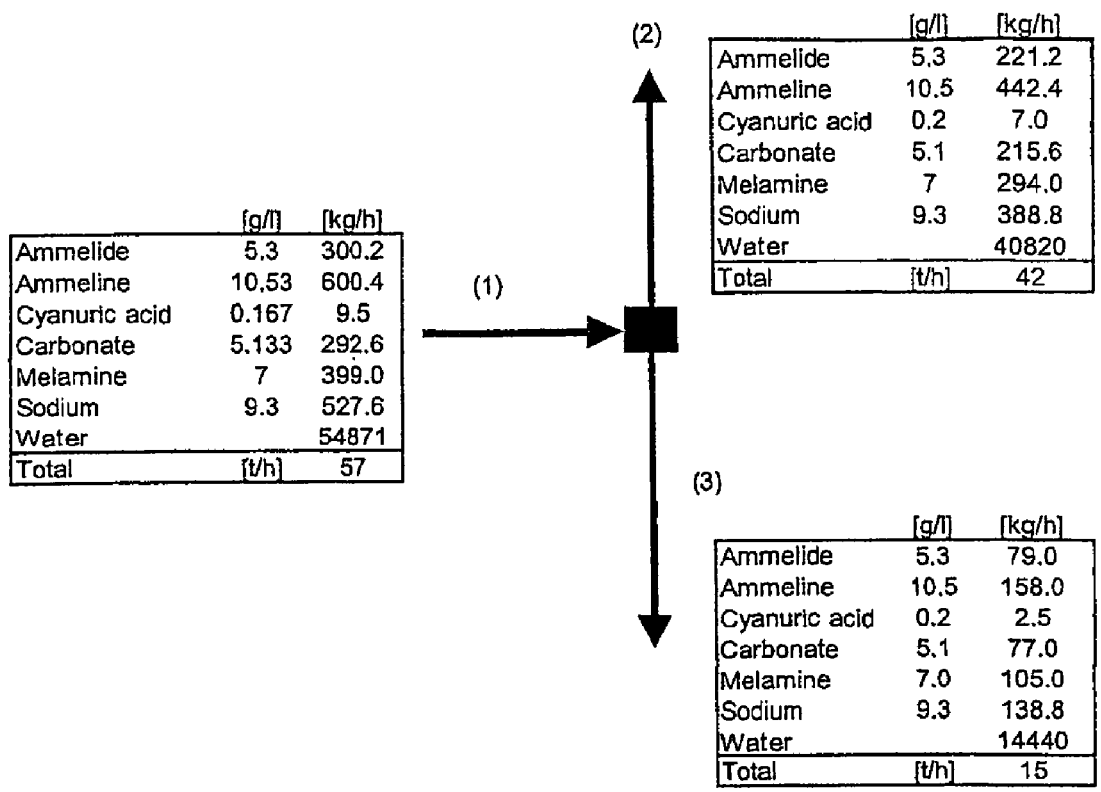
FIG. 1 shows a circulation of the triazine-containing water in a melamine plant which does not have a membrane filtration unit (state of the art)

The present invention accordingly provides a process for treating triazine-containing water of a melamine plant which is characterized in that
   the water comprising ionic and nonionic triazines in dissolved form is fed to at least one membrane filtration unit (MF),
   the water is separated in the membrane filtration unit (MF) into a fraction rich in ionic triazines and a fraction rich in nonionic triazines,
   then the fraction rich in ionic triazines is discharged and the fraction rich in nonionic triazines is recycled into the melamine plant.

The water treated in the process according to the invention can stem from any melamine source.

The water comprises both ionic and nonionic triazines, and generally has a basic pH.

The ionic triazines include, for example, the salts of the OATs, generally the sodium salts of ammeline, ammelide and cyanuric acid. In addition, further ionic compounds, for example carbonates, and/or cations such as sodium or ammonium may be present in the water.

The nonionic triazines present in the water are, for example, melamine, ureido-melamine or cyanuric acid. Other nonionic constituents, for example urea or further nitrogen compounds, may likewise be present.

What is crucial is that the substances are present for the most part in dissolved form in the water. In the case that too many solid constituents are present, there is the risk of membrane blockage. Since the solubility of the ingredients is dependent upon the pH, the pH can optionally be increased by adding alkali until complete solubility is achieved before the water is fed to the membrane filtration unit.

Advantageously, the membrane filtration unit consists of a membrane module, a pressure tube, a high-pressure pump, a reservoir and collecting vessel, and a circulation pump, the membrane modules advantageously being designed as wound modules.

The membrane filtration unit may comprise one or more filtration stages. In a multistage membrane filtration unit, the permeate of the first membrane filtration unit is fed to at least one further membrane filtration unit. In a multistage filtration, higher purities of the permeate are achieved. It is also possible in a multistage membrane filtration unit to use membrane modules with different separation properties. In this way, it is possible to achieve optimal degrees of separation according to the composition of the triazine-containing water. The retentates of the individual membrane filtration units can be combined or each fed alone to its further use.

In the membrane filtration unit, the water is separated into two fractions. The membrane filtration is advantageously a pressure filtration, the fractions being separated by means of the ionic properties of the constituents. The higher the pressure employed, the higher the throughput through the membrane filtration unit.

Downstream of the membrane filtration unit, the fraction rich in ionic triazines, which comprises a majority of the undesired OATs, is discharged. For example, it is fed to a thermal wastewater treatment unit in which the OATs are degraded.

The fraction rich in nonionic triazines, especially in melamine, downstream of the membrane filtration unit, can be recycled into any process stage of the melamine plant. It is recycled, for example, into the quencher, into the delay reactor or into the crystallizer of the wet part of a high-pressure melamine plant. In the case of a multistage membrane filtration plant, it is also possible to recycle at least some of the water partly purified after the first filtration stages actually into the melamine plant. It can be used there, for example, as washing water. The recycling of the melamine-containing water increases the melamine yield of the overall process.

The triazine-containing water preferably comprises the mother liquor obtained from aqueous solution in the melamine crystallization and has a pH of from 11 to 13. The use of the crystallization mother liquor for the process according to the invention gives rise to the greatest possible efficiency, since the mother liquor has a particularly high concentration of ionic and nonionic triazines.

In addition, the triazine-containing water may also comprise washing or rinsing solutions from any parts of the melamine plant. For example, washing solutions from the melamine filtration connected downstream of the melamine crystallization may be used. It is also possible to mix the crystallization mother liquor stream with washing and/or rinsing solutions before it is fed to the membrane filtration unit.

The fraction rich in ionic triazines, especially sodium salts of ammelide and ammeline, is preferably present in the retentate, while the fraction rich in non-ionic triazines, especially melamine, is preferably present in the permeate. This can be achieved by virtue of appropriate selection of the membrane type which offers retention selectively to ionic components.

Preference is given to an embodiment in which the membrane filtration unit is designed as a nanofiltration or reverse osmosis. Both in nanofiltration and in reserve osmosis, the separation is based on the principle of solution diffusion. The nanofiltration is effected at pressures up to about 40 bar. In reverse osmosis, a pressure of up to about 100 bar, which is above the osmotic pressure of the solution, is expended externally, in order to achieve the separation between the ionic and the nonionic constituents.

Preference is given to an embodiment in which the membrane is a composite membrane formed from a plurality of material layers. Composite membranes consist typically of a carrier material layer on which one or more thin membrane layers have been applied; an example thereof is that of so-called thin-film membranes. Such composite membranes ensure a good mechanical and chemical stability of the membrane.

The membrane may either be a flat surface or a wound surface. Wound membrane surfaces are preferred, since a high throughput based on the volume can be achieved with them.

The membrane materials used are preferably commercial polymers such as polysulfones. Among the polysulfones, it is possible, for example, to use sulfonated polysulfones or polyether sulfones. It is also possible to use polyamide membranes. These membrane materials are stable with respect to the high pH values of the triazine-containing water and the temperatures existing in the membrane filtration. For the material selection of the membrane, as well as the chemical and thermal stability, it is crucial that the separating performance should remain substantially constant over the entire operating time.

In order to ensure a continuous reaction, two or more membrane filtration units may be used, in which case one of the filtration units in each case is in the cleaning cycle and the others are in operation. The membranes are cleaned, for example, by flushing with hot condensate or with specific cleaning solutions, for example sodium hydroxide solution.

The size of the membrane area can be used to control the throughput through the membrane filtration unit; the greater the area, the higher the throughput.

Preference is given to an embodiment in which an ultrafiltration is connected upstream of the membrane filtration unit, and the permeate of the ultrafiltration is fed to the membrane filtration unit. The ultrafiltration serves to deposit coarse constituents or floating substances present in the water. In this way, protection and hence increased lifetime of the membrane are achieved. The separating principle in ultrafiltration approximates to a mechanical filtration; it is effected at pressures up to about 5 bar.

The coarse constituents deposited in the ultrafiltration are, for example, fine melamine particles which can be recycled into the melamine plant.

In an advantageous embodiment, the triazine-containing water is fed to an ultrafiltration, the permeate of the ultrafiltration is fed to a nanofiltration, and the permeate of the nanofiltration is fed to a reverse osmosis. The advantage of this embodiment is that the membrane filtration unit is protected by the upstream ultrafiltration, and the series connection of two membrane filtration units achieves a high degree of separation with simultaneous mechanical deburdening of the individual filtration stages.

The membrane filtration unit is preferably operated at a temperature of from 20 to 95° C., more preferably from 50 to 70° C., and at a pressure of from 0.1 to 100 bar, more preferably at a pressure of from 10 to 30 bar. These parameters are controllable by technical means and afford a good separation result.

The concentration ratio of the nonionic triazines in the permeate:retentate downstream of the membrane filtration unit is preferably from 0.7 to 1.1. The higher the ratio, the less melamine loss can be achieved in the overall process. The concentration ratio of the ionic components in the permeate:retentate is advantageously from 0.0 to 0.9. The lower the ratio, the smaller the amount of by-products recycled into the melamine plant.

The concentration ratio reflects the degree of separation. A concentration ratio of 1:1 means that the concentration of one component in the permeate is just as high as in the retentate, and the degree of separation is accordingly 50%.

The concentration ratio can be influenced via the selection of the membrane material and membrane structure. It is also possible to combine different membrane types having different degrees of separation with one another in order to achieve the optimal result for a given separation problem.

In an advantageous embodiment, the mass ratio of permeate:retentate is 1.5 downstream of the membrane filtration unit. It is particularly advantageous when the mass ratio of permeate:retentate is from 1.5 to 20. This ensures that a large portion of the contaminated water is recycled into the melamine process after it has been cleaned in the membrane filtration unit. This causes a saving of fresh water in the melamine process.

The invention further provides a high-pressure process for preparing melamine from urea, characterized in that nonionic triazines, such as melamine, and ionic triazines in the triazine-containing water from a melamine process is fed to at least one membrane filtration unit and separated thereby into a fraction rich in ionic triazines and a fraction rich in nonionic triazines, then the fraction rich in ionic triazines is discharged into a plant for thermal wastewater treatment at >130° C., and the fraction rich in nonionic triazines is recycled into the wet part of the melamine plant.

It is possible to conduct all of the triazine-containing water or only a portion thereof into the membrane filtration unit. Typically, some of the triazine-containing water is recycled into the melamine plant without treatment in the membrane filtration unit, and a second portion is recycled after the inventive treatment in the membrane filtration unit.

In the thermal wastewater treatment, a decomposition of the ionic triazines and further constituents takes place, for example, in a hydrolyzer under high pressure and high temperature. The $CO_2$ and $NH_3$ formed can be recovered as ammonium carbonate and be recycled into the melamine or urea plant at a suitable point, while the cleaned water can be discharged for disposal.

Caused by the high recycling rate, the use of the inventive membrane filtration results in a lower hydraulic wastewater burden being introduced into the thermal wastewater treatment. This gives rise to a size reduction in the design of new wastewater plants and a capacity increase in existing wastewater plants.

In a preferred embodiment of the high-pressure process, the triazine-containing water is fed to an ultrafiltration, the permeate of the ultrafiltration is fed to the nanofiltration, and the retentate of the ultrafiltration is recycled together with the permeate of the nanofiltration into the melamine plant.

In this way, coarse constituents of the triazine-containing water can be deposited in the ultrafiltration, which ensures protection of the nanofiltration membrane.

The retentate:permeate ratio can be adjusted via the pressure of the ultrafiltration. This ratio determines the concentration of ionic triazines in the recycled triazine-containing water and hence in the triazine-containing water circuit of the melamine plant.

The process according to the invention for the treatment of triazine-containing water of a melamine plant achieves several advantages.

The specific separation between ionic triazines, such as melamine, and non-ionic triazines in the membrane filtration unit allows a majority of the melamine present in the triazine-containing water to be recycled into the process. This increases the yield over the overall melamine process. In addition, the concentration of undesired ionic triazines in the recycled stream is lowered. A low concentration of ionic triazines in the triazine-containing water circuit of the melamine plant is desired, since the fresh water demand in the workup part of the melamine plant is reduced in this way. In addition, the process can be performed in the liquid phase and continuously.

FIG. 1 shows a flow diagram without the process according to the invention, in which the separation of a triazine-containing water 1 is shown. The triazine-containing water stream 1 stems from a melamine plant which is not shown here. From the 57 t/h of triazine-containing water 1 which are obtained, 42 t/h, corresponding to 73% of the total amount of triazine-containing water, are recycled 2 into the aqueous workup of the melamine plant without treatment in a membrane filtration unit. The remaining 15 t/h, corresponding to 27% of the triazine-containing amount of water, are discharged 3 into a wastewater plant. There, the constituents are decomposed by thermal hydrolysis and the resulting cleaned water is subsequently disposed of.

Since the two triazine-containing water streams, as is evident from FIG. 1, have the same concentration of constituents, the discharge into the wastewater plant is accompanied by a relatively large melamine loss, specifically 105 kg/h. On the other hand, the amount of by-products introduced back into the process via the recycled triazine-containing water stream together with the melamine, at a total of 886.2 kg/h of ammelide, ammeline, cyanuric acid and carbonate, is considerable.

This amount of recycled by-products limits the maximum amount of triazine-containing water recyclable in a process according to FIG. 1.

In the aqueous workup part of the melamine plant, all by-products are removed from the melamine melt coming from the high-pressure part. This is done by selectively crystallizing the melamine out, while the by-products are dissolved quantitatively in the crystallization mother liquor. For the quantitative removal, it is necessary that the saturation concentration of by-products in the triazine-containing mother liquor is not exceeded, otherwise the melamine which has crystallized out would be contaminated with by-products.

Since the triazine-containing water stream recycled into the aqueous workup part is already saturated in by-products, a sufficient amount of fresh water has to be supplied to the process in order to ensure the quantitative dissolution of the additional by-products from the melamine melt.

Figure 2:
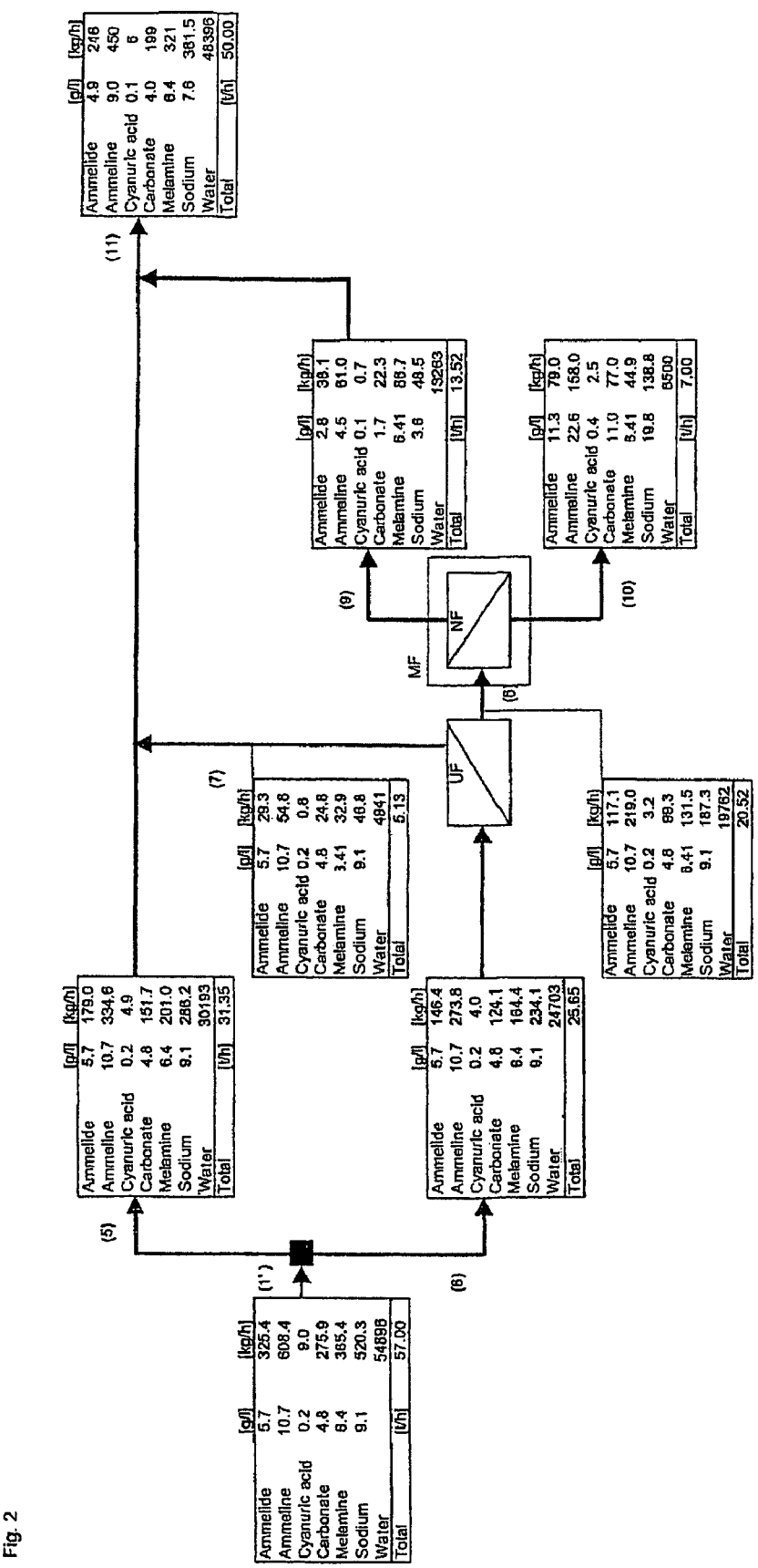
FIG. 2 shows a circulation of the triazine-containing water in a melamine plant which has a nanofiltration with upstream ultrafiltration.

In one embodiment of the invention, which is shown in FIG. 2, 57 t/h of a triazine-containing water 1' are obtained in the melamine process, which has virtually the same concentration of constituents as that from the process described in FIG. 1.

31.4 g/h of this triazine-containing water, corresponding to 55% of the total amount, are recycled into the melamine process without treatment as a bypass stream 5 analogously to the process according to FIG. 1. 25.7 t/h, corresponding to 45% of the triazine-containing water 6, are fed to an ultrafiltration unit UF. In the ultrafiltration unit UF, floating substances and relatively large particles which are present in the triazine-containing water are removed. These are present in the retentate 7 of the ultrafiltration and are recycled into the process together with stream 5. The separating principle of ultrafiltration is based exclusively on particle size; with regard to the concentration of the constituents, the ultrafiltration does not result in any change.

The permeate 8 of the ultrafiltration is fed to a membrane filtration unit MF (shown with dashed lines in FIG. 2), which has a nanofiltration NF here. Like reverse osmosis and ultrafiltration, the nanofiltration NF is a pressure-driven membrane process for separating dissolved components, especially from aqueous solutions. With regard to its separating performance, the nanofiltration should be placed between reverse osmosis and ultrafiltration. A special feature of nanofiltration membranes is their high ion selectivity. Salts with monovalent ions pass through the membrane to a high degree. Salts with polyvalent ions are retained to a higher degree.

The membrane filtration unit MF serves for separation into a fraction which is rich in ionic triazines and a fraction which is rich in nonionic triazines.

The membrane used in the nanofiltration NF is a composite membrane; the temperature was 60° C.; the pressure in the nanofiltration was 20 bar. 13 t/h of permeate 9 and 7 t/h of retentate 10 are obtained. While the permeate 9 is recycled into the melamine plant together with the retentate 10 of the ultrafiltration 7 and the bypass stream 5, the retentate 10 of the nanofiltration NF is discharged into the wastewater plant.

The permeate/retentate ratio of the nanofiltration is 1.9/1. While the concentration of nonionic melamine after the nanofiltration NF is unchanged, the permeate 9 has a lower concentration of ionic ammelide, ammeline, cyanuric acid and carbonate than in the feed stream 8. Compared to the feed, the retentate 10 has a correspondingly higher concentration of ionic compounds.

Since the concentration of by-products in the discharged retentate 10, with the same absolute amount of by-products to be removed, is higher than in the comparative process from FIG. 1, the amount of hydraulic wastewater, at 7 t/h, is lower by more than half than in the comparative process. This means a lower burden on the wastewater plant, whose capacity rises as a result. The reduced by-product concentration in the recycled permeate 9 allows a larger amount of triazine-containing water to be recycled 2' into the melamine process; this is 50 t/h in comparison to 42 t/h in the comparative process. In this way, a saving of fresh water in the melamine plant is achieved. Owing to the higher melamine concentration in the recycled stream 2', 321 kg/h of melamine can be recovered, while 294 kg/h are recycled in the comparative process.

For the process according to the invention, this means a rise in the melamine yield.

The invention claimed is:

1. A process for treating triazine-containing water of a melamine plant, comprising the steps of:
   feeding a water comprising ionic and nonionic triazines in dissolved form to at least one membrane filtration unit,
   separating the water in the membrane filtration unit into a fraction rich in ionic triazines and a fraction rich in nonionic triazines,
   discharging the fraction rich in ionic triazines and recycling the fraction rich in nonionic triazines into the melamine plant.

2. The process as claimed in claim 1, wherein, downstream of the membrane filtration unit, the fraction rich in ionic triazines is present in retentate and the fraction rich in nonionic triazines in permeate.

3. The process as claimed in claim 1, wherein the fraction rich in ionic triazines comprises sodium salts of ammeline and ammelide.

4. The process as claimed in claim 1, wherein the fraction rich in nonionic triazines comprises melamine.

5. The process as claimed in claim 1, wherein the membrane filtration unit comprises at least one filtration stage.

6. The process as claimed in claim 1, wherein the membrane filtration unit is at least one of a nanofiltration and reverse osmosis.

7. The process as claimed in claim 1, wherein the membrane filtration unit is comprised of a composite membrane formed from a plurality of material layers.

8. The process as claimed in claim 7, wherein the membrane is a wound surface.

9. The process as claimed in claim 7, wherein the membrane materials are polysulfones.

10. The process as claimed in claim 1, wherein an ultrafiltration is connected upstream of at least one membrane filtration unit and permeate of the ultrafiltration is fed to the membrane filtration unit.

11. The process as claimed in claim 1, wherein the triazine-containing water from the melamine process is fed to an ultrafiltration, permeate of the ultrafiltration is fed to a nanofiltration and permeate of the nanofiltration is fed to a reverse osmosis.

12. The process as claimed in claim 1, wherein the triazine-containing water comprises melamine crystallization mother liquor.

13. The process as claimed in claim 1, wherein the triazine-containing water has a pH of from about 11 to 13.

14. The process as claimed in claim 1, wherein the membrane filtration unit is operated at a temperature of from about 20 to 95° C.

15. The process as claimed in claim 13, wherein the membrane filtration unit is operated at a temperature of from about 50 to 70° C.

16. The process as claimed in claim 1, wherein the membrane filtration unit is operated at a pressure of from about 0.1 to 100 bar.

17. The process as claimed in claim 14, wherein the membrane filtration unit is operated at a pressure of from about 10 to 30 bar.

18. The process as claimed in claim 2, wherein, downstream of the membrane filtration unit, the concentration ratio of the nonionic triazines in the permeate:retentate is from 0.7 to 1.1.

19. The process as claimed in claim 2, wherein, downstream of the membrane filtration unit, the concentration ratio of the ionic components in the permeate:retentate is from 0.0 to 0.9.

20. The process as claimed in claim 2, wherein, downstream of the membrane filtration unit, the mass ratio of permeate:retentate is 1.5.

21. The process as claimed in claim 18, wherein, downstream of the membrane filtration unit, the mass ratio of permeate:retentate is from 1.5 to 20.

22. A high-pressure process for preparing melamine from urea, wherein triazine-containing water from a melamine process is fed to at least one membrane filtration unit and separated thereby into a fraction rich in ionic triazines and a fraction rich in nonionic triazines, then the fraction rich in ionic triazines is discharged into a plant for thermal wastewater treatment at >130° C., and the fraction rich in nonionic triazines is recycled into a wet part of a melamine plant.

23. The high-pressure process as claimed in claim 22, wherein the triazine-containing water is fed to an ultrafiltration, the permeate of the ultra-filtration is fed to a nanofiltration, and the retentate of the ultrafiltration is recycled together with permeate of the nanofiltration into the melamine plant.

* * * * *